US012708341B2

(12) United States Patent
Lichy et al.

(10) Patent No.: US 12,708,341 B2
(45) Date of Patent: Aug. 18, 2026

(54) METHOD AND CONTROL FACILITY FOR CONTROLLING A COMPUTED TOMOGRAPHY SYSTEM

(71) Applicant: Siemens Healthineers AG, Forchheim (DE)

(72) Inventors: Matthias Lichy, Nuremberg (DE); Bernd Hofmann, Erlangen (DE); Claudia Lindner, Nuremberg (DE); Bernhard Schmidt, Fuerth (DE)

(73) Assignee: SIEMENS HEALTHINEERS AG, Forchheim (DE)

( * ) Notice: Subject to any disclaimer, the term of this patent is extended or adjusted under 35 U.S.C. 154(b) by 0 days.

(21) Appl. No.: 18/796,828

(22) Filed: Aug. 7, 2024

(65) Prior Publication Data

US 2025/0049411 A1 Feb. 13, 2025

(30) Foreign Application Priority Data

Aug. 10, 2023 (EP) .................................... 23190831

(51) Int. Cl.

| | |
|---|---|
| ***A61B 6/00*** | (2024.01) |
| ***A61B 6/03*** | (2006.01) |
| ***G06T 12/10*** | (2026.01) |

(52) U.S. Cl.

CPC .............. *A61B 6/547* (2013.01); *A61B 6/032* (2013.01); *G06T 12/10* (2026.01); *G06T 2210/41* (2013.01); *G06T 2211/424* (2013.01)

(58) Field of Classification Search

CPC ....... A61B 6/547; A61B 6/032; A61B 6/5205; A61B 6/5258; A61B 6/54; A61B 6/502;

(Continued)

(56) References Cited

U.S. PATENT DOCUMENTS 5,544,212 A * 8/1996 Heuscher .............. G01T 1/2985 378/15
6,130,930 A * 10/2000 Tam ..................... A61B 6/4085 378/94

(Continued)

FOREIGN PATENT DOCUMENTS

CN 103961123 A 8/2014
DE 102007033883 A1 1/2009

(Continued)

OTHER PUBLICATIONS

Extended European Search Report and English translation thereof for European Application No. 23190831.0 mailed Feb. 12, 2024.

(Continued)

*Primary Examiner* — Kiho Kim
(74) *Attorney, Agent, or Firm* — Harness, Dickey & Pierce, P.L.C.

(57) ABSTRACT

One or more example embodiments relates to a method for controlling a computed tomography system, the method comprising defining an examination region of an examination object; defining a number of interfering structures, wherein an interfering structure is a structure located within a beam path of the computed tomography system and reflects or absorbs X-ray radiation with a strength outside of a tolerance range; calculating beam paths of X-rays of a CT examination of the examination region and ascertaining interference angle ranges of a gantry of the computed tomography system at which the beam paths run through the interfering structure and the examination region; carrying out a CT scan while the gantry rotates, and recording CT data; reconstructing an image dataset from CT data of the recorded CT data excluding the ascertained interference angle ranges; and outputting the image dataset.

18 Claims, 2 Drawing Sheets

(58) Field of Classification Search
CPC . A61B 6/5252; G06T 11/005; G06T 2210/41; G06T 2211/424
See application file for complete search history.

(56) References Cited

U.S. PATENT DOCUMENTS

| | | | | |
|---|---|---|---|---|
| 6,333,960 | B1 * | 12/2001 | Tam ....................... | A61B 6/027 378/15 |
| 2007/0083101 | A1 | 4/2007 | Rietzel | |
| 2010/0183115 | A1 | 7/2010 | Van Stevendaal et al. | |
| 2012/0128120 | A1 | 5/2012 | DeMan et al. | |
| 2014/0211912 | A1 | 7/2014 | Wang et al. | |
| 2017/0340268 | A1 | 11/2017 | Danielsson et al. | |
| 2022/0071578 | A1 | 3/2022 | Schildkraut et al. | |

FOREIGN PATENT DOCUMENTS

| | | | |
|---|---|---|---|
| DE | 102011055616 | A1 | 7/2012 |
| EP | 1764040 | A2 | 3/2007 |
| WO | WO 2020142404 | A1 | 7/2020 |

OTHER PUBLICATIONS

European Communication under Rule 71(3) and English translation thereof for European Application No. 23190831.0 mailed Feb. 21, 2025.

* cited by examiner

METHOD AND CONTROL FACILITY FOR CONTROLLING A COMPUTED TOMOGRAPHY SYSTEM

CROSS-REFERENCE TO RELATED APPLICATION(S)

The present application claims priority under 35 U.S.C. § 119 to European Patent Application No. 23190831.0, filed Aug. 10, 2023, the entire contents of which is incorporated herein by reference.

FIELD

One or more example embodiments relates to a method and to a control facility for controlling a computed tomography system and to a computed tomography system ("CT system").

RELATED ART

In CT examinations of locally limited anatomy ("CT": computed tomography), for example the chest, an inadequate number of projection angles is captured for the desired represented anatomy with conventional recording technology and image reconstruction. Specifically, projections through the spinal column would be used for representing the chest, axilla and front thorax wall, and these can have a high dose and be encumbered by artifacts, moreover. They can have beam hardening artifacts, for example.

Furthermore, the use of dedicated positioning aids (compression-free, "hanging" representation of the parenchyma) is necessary, in particular in the case of (female) breast imaging. However, these cause a suboptimum positioning of the female patient for conventional data acquisition and data reconstruction (off-center positioning).

A reduction in the image quality also occurs for a range of examinations without dedicated positioning aid, for example lateral positioning in the case of liver intervention.

The cross-sectional techniques (for example flat-panel CT) carried out for monitoring interventions and radiotherapy positioning exhibit the same basic problem and differ only in the issue of the pronounced cone beam projection compared to conventional CT technology. With regard to the CT-based breast imaging cited by way of example, there exists a dedicated chest CT. With the technique applied in this connection, representation of the thorax wall and the axilla is not possible owing to the technical and physical conditions of the system. Similarly, a simultaneous representation of the two breasts is not possible, and for dynamic examinations (for example contrast agent dynamic) this potentially has adverse effects on clinical use. Furthermore, simultaneous imaging and accessibility to the breast for interventions, as is achieved in MRI, is not currently possible with such a system.

At present, individually based positioning aids are simply used to counteract the problem. In the field of CT-based breast imaging there are, similar to MRI, custom-built positioning aids for imaging or, in the case of dedicated breast scanners, corresponding constructional measures for placement of the breasts.

SUMMARY

One or more example embodiments provides an alternative, more convenient method and a corresponding apparatus for controlling a computed tomography system with which the above-described drawbacks are avoided.

This is achieved by a method as claimed in claim 1, a control facility as claimed in claim 10 and a computed tomography system as claimed in claim 12.

BRIEF DESCRIPTION OF THE DRAWINGS

One or more example embodiments will be explained in detail below with reference to the accompanying figures. Identical components are provided with identical reference numerals in the different figures. As a rule, the figures are not to scale. In the drawings.

DETAILED DESCRIPTION

Figure 1:
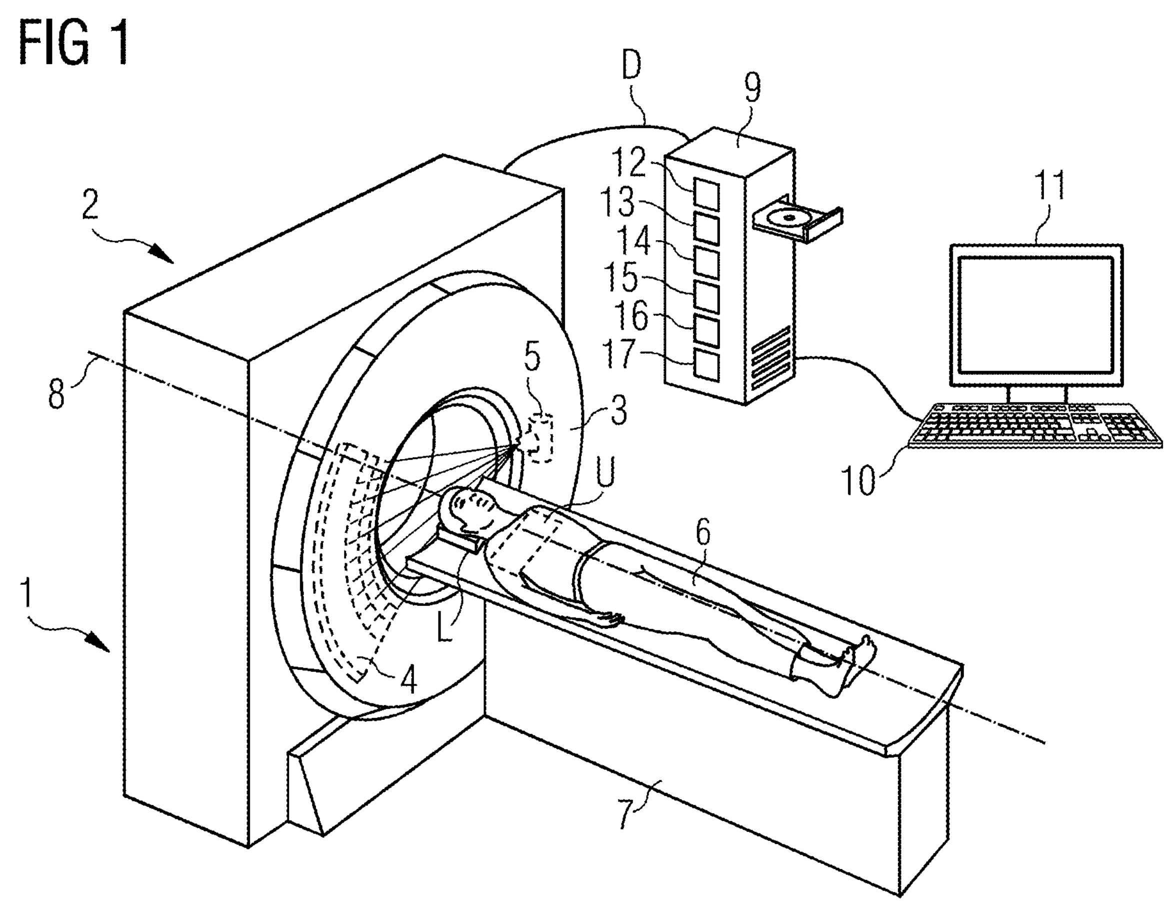
FIG. 1 shows a rough schematic representation of a CT system with an exemplary embodiment of an inventive control facility for carrying out the method.

One or more example embodiments serves for controlling a computed tomography system. It allows an improvement in the image quality and provides, moreover, a dose reduction for the patient, in particular when high-resolution CT techniques, such as photon-counting technology, is used. It is precisely in the recording of anatomical regions in which a high resolution with simultaneously low contrast behavior are advantageous for a diagnostic statement that the method provides monitoring of image artifacts with simultaneously comparatively low radiation dose.

The method comprises the following steps:

- defining an examination region of an examination object,
- defining a number of interfering structures, wherein an interfering structure is a structure which is located within the beam path of the computed tomography system and reflects or absorbs X-ray radiation with a strength outside of a tolerance range,
- calculating the beam paths of the X-rays of a CT examination of the examination region and ascertaining interference angle ranges of a gantry of the computed tomography system at which beam paths run through an interfering structure and the examination region,
- carrying out a CT scan while the gantry rotates, and recording CT data,
- reconstructing an image dataset from the CT data with the omission of ascertained interference angle ranges,
- outputting the image dataset.

The examination object can theoretically be an arbitrary body and the examination region a part of this body or the entire body. Preferably, the examination object is a person and the examination region is an organ or a region of the body. The examination region is typically defined before the examination.

A number of interfering structures is also defined in preparation for the examination. This can be a single structure but also a plurality of structures. An interfering structure is located within the beam path of the computed tomography system, i.e. is impinged on by X-ray radiation and reflects or absorbs it. It is not arbitrary structures that are regarded as interfering structure, however, rather only those whose reflection or absorption has a strength outside of a tolerance range, for example lie above or below a predefined limit value. The tolerance range or corresponding materials and dimensions for structures are defined in advance. In the case of a person, bone material, for example, can be interfering and larger bones, such as, in particular, the spinal column, can be regarded as interfering structures. However, parts of the couch or positioning aids could also be regarded as interfering structures. Basically a health professional knows which structures can interfere with the images. These structures can then be defined as "interfering structures" for the method. Preferred interfering structures have a known position in the body or in the region of the examination and are image regions with high Hounsfield units. However, air can also constitute an interfering structure. In this case image regions with the lowest Hounsfield units are preferred as interfering regions.

If the interfering structures are known, then basically their position is also known. In the case of a person the bone structure, for example, is known and the position of the spinal column can be easily specified as an exemplary interfering structure even if it is not possible to look into the person (at this point in time).

With the known position of the interfering structure and the defined position of the examination region beam paths of the X-rays of a CT examination can now be calculated. Let it be noted that the X-ray source is still switched off. Only the theoretical paths are determined. It is preferred that the patient (or the examination object) is positioned such that the number of interfering structures is (clearly) located eccentrically of the isocenter.

Using the calculated beams paths it is then determined whether they run through an interfering structure and the examination region. The angle at which the X-ray source would emit X-rays which run through an interfering structure and the examination region is referred to as the "interference angle" and the range of the interference angle as the "interference angle range". The interference angle ranges are therefore those angle ranges which the rotating gantry can assume in which X-rays would be emitted which run through an interfering structure and the examination region. It can preferably be tolerated if an X-ray would run through the interfering structure only after passing through the examination region. These angle ranges can therefore preferably not be regarded as interference angle ranges.

Once the interference angle ranges are defined a CT scan can then be carried out with a rotating gantry and CT data (i.e. basically images) can be recorded in the process.

An image dataset is then reconstructed from this CT data. Ascertained interference angle ranges are omitted. Let it be noted that it is not imperative for all interference angle ranges to be omitted. For example, when two separate examination regions exist, a first interference angle range can be omitted for the reconstruction of a first image dataset of the first examination region and a second interference angle range can be omitted for the reconstruction of a second image dataset of the second examination region.

A reduction in the dose can be achieved in that during the recording an X-ray source is switched off in the interference angle ranges.

The reconstructed image dataset is then output. For example it can be displayed for a direct diagnosis or be stored for a later diagnosis.

Therefore the method basically cuts areas out of the possible CT data which would impair the image. It should be noted in this regard that a recording angle of slightly more than 180° is typically required for a reconstruction. It is therefore advantageous if in the case of opposing interference angle ranges, that angle range at which the interference is less is not regarded as the interference angle range. Alternatively or in addition, CT data can also be simulated for interference angle ranges or be calculated (for example with appropriately trained AI) and used for the reconstruction.

With the interference angle ranges, the necessary projections can be defined for the examination region while avoiding image quality-limiting and thus dose-inefficient projections. Specifically, for example beam paths through the bony spinal column are avoided. This can occur for sequential as well as for helical recordings.

The inventive control facility for controlling a computed tomography system is preferably designed for carrying out the inventive method. It comprises the following components:

an examination unit designed for defining an examination region of an examination object, an interfering structure unit designed for defining a number of interfering structures, wherein an interfering structure is a structure which is located within the beam path of the computed tomography system and reflects or absorbs X-ray radiation with a strength outside of a tolerance range, a calculation unit designed for calculating the beam paths of the X-rays of a CT examination of the examination region and ascertaining interference angle ranges of a gantry of the computed tomography system at which beam paths run through an interfering structure and the examination region, a data interface designed for outputting control commands for carrying out a CT scan while the gantry rotates, and for receiving CT data, a reconstruction unit designed for reconstructing an image dataset from the CT data with the omission of ascertained interference angle ranges, a data interface designed for outputting the image dataset.

The function of the components was described in detail above in the context of the inventive method.

An inventive computed tomography system comprises an inventive control facility or is alternatively or additionally designed for carrying out the inventive method. Preferably, the CT system comprises a flat panel detector.

The majority of the above-mentioned components of the control facility can be wholly or partially implemented in the form of software modules in a processor of a corresponding computing system. An implementation largely in terms of software has the advantage that even previously used computing systems can be easily retrofitted by way of a software update in order to work inventively. In this regard the object is also achieved by a corresponding computer program product with a computer program which can be loaded directly into a computing system, with program segments in order to execute the steps of the inventive method, at least the steps which can be executed by a computer, when the program is executed in the computing system. Apart from the computer program, such a computer program product can potentially comprise additional component parts, such as documentation and/or additional components, also hardware components, such as hardware keys (dongles, etc.) in order to use the software.

It should be noted that carrying out a CT scan corresponds to the transmission of corresponding control commands and the receiving of CT data. The method can be computer-implemented, in particular.

A computer-readable medium, for example a memory stick, a hard disk or another transportable or permanently installed data carrier, can serve for transport to the computing system or the control facility and/or for storage on or in the computing system or the control facility, on which medium the program segments of the computer program, which can be read-in and executed by a computing system, are stored. For this the computing system can have, for example, one or more cooperating microprocessor(s) or the like.

Further, particularly advantageous embodiments and developments of the invention can be found in the dependent claims and the following description, wherein the claims of one category of claims can also be developed analogously to the claims and descriptive parts relating to a different category of claims and, in particular, individual features of different exemplary embodiments or variants can also be combined to form new exemplary embodiments or variants.

According to a preferred method, the CT data is recorded with the omission of ascertained interference angle ranges. It is preferred that an X-ray source used for recording is switched off in interference angle ranges or at least its radiant power is reduced. The overall dose is reduced as a result. Preferably, a dose is modulated with a change in beam parameters, for example kV setting or reference mAs.

If there is a desire to improve the images while the overall dose remains the same, then beam parameters, in particular the acceleration voltage and/or the current strength of the X-ray source, are preferably determined for the entire recording on the basis of an entire angle range of 360° minus the interference angle ranges.

According to a preferred method, the interference angle range is regarded as an angle range at which beams of an X-ray source of the gantry firstly run through an interfering structure and thereafter through the examination region. Since the beam is usually conical, these interference angle ranges have a serious effect on the recordings as the respectively opposing angle ranges at which the X-ray radiation firstly passed through the examination region and only thereafter impinge on the interfering structure. The latter angle ranges can then be regarded as the angle ranges which are to be used for a reconstruction (and recording).

According to a preferred method, defining an interfering structure is based on a topogram of the examination object, a camera recording of the examination object or a model of the examination object.

The examination object is preferably a human or animal body and an interfering structure a bone, a positioning aid or a part of the gantry.

According to a preferred method, the examination object is positioned via a positioning aid. An interfering structure is then defined preferably on the basis of a position and a form of the positioning aid. The positioning aid is therefore an interfering structure in this case. It is preferred that the isocenter of the examination region is defined after positioning of the examination object via the positioning aid. The isocenter is preferably defined automatically via an image recognition or via a communication between positioning aid and computed tomography system.

According to a preferred method, the examination object is fixed via a fixation. Defining an interfering structure is then preferably based on a position and a form of the fixation. In this case the fixation, for example a screw, a plate or another rigid body, is therefore an interfering structure. The interfering structure is preferably also defined automatically here via an image recognition or via a communication between fixation and computed tomography system.

In practice, after a dedicated positioning aid has been introduced into the scanner via a manual input, image recognition or by way of the direct communication between positioning aid and scanner, the new isocenter can be calibrated in relation to the anatomy of interest. In the case of a chest representation, a predefined target region could be communicated to the CT scanner, for example the volume of the rib cage, or the position or extent of the chest. The same applies to a fixation.

In this respect a preferred control facility comprises a position unit designed for ascertaining a position of a positioning aid and/or fixation. It is preferred that the position unit is designed to estimate the position on the basis of images and/or receive and evaluate items of information of the positioning aid.

According to a preferred method, by considering the entire angle range of 360° minus the interference angle ranges it can be checked during the course of ascertaining the interference angle ranges whether the remaining angle range overlaid with the remaining angle range rotated about 180° has a continuous angle range of 360°. Therefore it is basically checked whether at least 180° are available for a reconstruction. Let it be noted that this checking does not necessarily have to take place by way of rotating and overlaying a copy of the remaining angle range. However, if the remaining angle range has a complicated structure, this checking process would be advantageous. If gaps should be present in the case of such an overlaying, then 180° are not available for reconstruction, i.e. items of information are missing in this case.

It is preferred that in the case where the remaining angle range is less than 360°, a missing angle range, simulated data, which simulates recordings in the missing angle range, is added to the CT data before reconstruction of the image dataset. Alternatively or in addition, a missing angle range can be removed from the number of interference angle ranges since the interference angle ranges are indeed already known before a recording. For this it is preferred that a degree of interference in the missing angle range and an angle range rotated 180° thereto is ascertained and that angle range which has the smaller degree of interference is removed from the interference angle ranges. This is preferably that angle range at which the X-ray first passes through the examination region and only then impinges on the interfering structure.

According to a preferred method, two or more examination regions of the examination object are defined. Interference angle ranges for both examination regions are preferably separately ascertained. An interference angle range is associated with an examination region when beam paths run through an interfering structure and the relevant examination region. An image dataset is then reconstructed separately with the omission of ascertained interference angle ranges of the relevant examination region for each examination region. If, therefore, an interfering structure, for example, is defined and there is a first interference angle range for the first examination region and a second interference angle range for the second examination region, the image dataset is then reconstructed for the first examination region with the omission of the first interference angle range and the image dataset for the second examination region with the omission of the second interference angle range.

It is preferably ascertained which interference angle ranges associated with the examination regions are identical. The CT data can then be recorded with the omission of the identical interference angle ranges. If it is possible for a plurality of examination regions to exist, the respective interference angle ranges can be disjunct. The X-ray source should then not be switched off in an interference angle range because then insufficient data could be available for an examination region for the reconstruction. If there is a shared interference angle range, however, then the X-ray source can be switched off in order to reduce the overall dose. Therefore, an X-ray source used for recording is preferably switched off in the identical interference angle ranges or at least its radiant power is reduced.

An optimization can consequently occur for multiple areas to be examined. For example, a contrast agent dynamic of both breasts would require a different number of projections for the image acquisition than for the individual representation of a breast lesion which is to be biopsied. Irrespective thereof, reconstruction takes place separately, preferably on the basis of the optimum projections for the individual target volumes.

It is also preferred that an image dataset is reconstructed from two different projection sets. In the example of the contrast agent dynamic, the acquisition could be optimized to the need for simultaneous acquisition of both breasts. The image reconstruction can preferably be based on individual optimized projections which can then be combined again into one image. Two different interference angle ranges can exist for these different projection sets, so the features for two examination regions can be applied to this too.

According to a preferred method, a combination of a data sparsity reconstruction technique and an iterative solution approach is used during reconstruction of an image dataset. An addition of projections is preferred for representing structures, in particular of biopsy needles, without the need for complete data acquisition, as is necessary for the detailed representation of breast tissue. Such methods are known in the prior art and are used, for example, in CT for calculating data outside of the areas completely captured by the detectors (extended field of view). These techniques are particularly advantageous for the inventive method if the X-ray source is switched off in interference angle ranges, i.e. no CT data is recorded from there.

According to a preferred method, the examination region is the chest or the lungs. A preferred interfering structure is the spinal column.

It should be noted that an interfering structure does not necessarily have to absorb or reflect a lot of radiation, and instead, depending on the type of examination, an interfering structure can also reflect or absorb a particularly small amount of radiation (i.e. less than a predefined limit value). For example, in the case of a biopsy of a bone process in the iliac crest, projections are preferred which include a lot of information about the bone with the omission of projections with a lot of soft tissue information. Interfering structures could be defined here using a priori knowledge and/or topograms.

A combination of conventional dose modulation with a selective projection selection (omitting interference angle ranges) is also preferred for the dedicated reconstruction (for example zoomed spinal column). An improvement in the image quality while preserving beam efficiency can consequently be achieved. The method could also be used [as] a replacement or as a supplement to previous approaches to improving image quality. For example, on the basis of the information of a topogram a foreign body could be identified in the examination object and this could be defined as an interfering structure. Then, interference angle ranges can be defined for this foreign body, for example in order to prevent artifacts, for example metal artifacts. For example, in the case of a lung representation, the projections could be omitted on the basis of a foreign body which has penetrated into the lungs. This constitutes a significant difference from iterative artifact reduction since in the proposed methods precise knowledge already exists with the introduced foreign body and prospective projections can be separated out.

FIG. 1 shows an embodiment of a computed tomography system (CT system) 1 with a radiation detector 4 and a radiation source 5. The radiation source 5 is embodied to expose the radiation detector 4 to radiation. The CT system 1 shown comprises a gantry 2 with a rotor 3. The rotor 3 comprises as a radiation source 5 an X-ray source 5 and the radiation detector 4, which is embodied to detect X-ray radiation.

The rotor 3 can be rotated about the rotational axis 8. The patient 6 is positioned on the couch 7 and can be moved along the rotational axis 8 by the gantry 2. The head of the patient 6 is bedded on a positioning aid L. The computing unit 9 is provided for controlling the imaging system 1 and/or for generating an image dataset on the basis of signals detected by the radiation detector 4.

A (raw) X-ray image dataset of the examination object 6 is customarily recorded from a large number of angle directions via the radiation detector 4 with one beam energy respectively, i.e. two or more raw datasets. A (final) image dataset can then be reconstructed on the basis of the (raw) X-ray image dataset via a mathematical method, for example comprising a filtered back projection or an iterative reconstruction method.

The computing unit 9 serves here as a control facility 9 for controlling the CT system 1. An input facility 10 and an output facility 11 are connected to this computing unit 9. The input facility 10 and the output facility 11 can enable, for example, an interaction by way of a user or the representation of a generated image dataset B.

Figure 3:
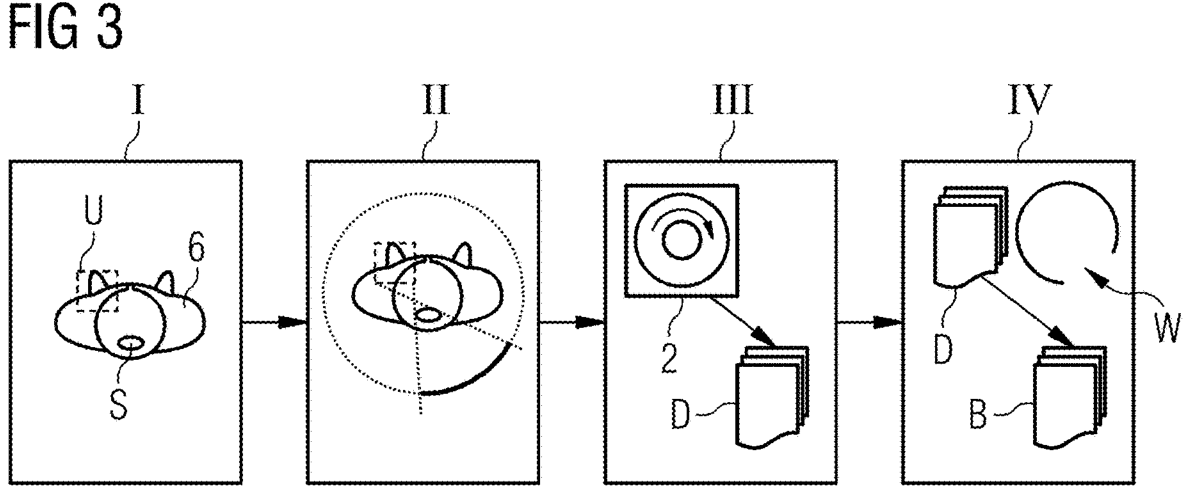
FIG. 3 shows a sequence plan for one possible sequence of an inventive method according to one or more example embodiments.

The control facility 9 comprises here a data interface 12 for receiving CT data, for outputting control commands and for outputting reconstructed image datasets (see also FIG. 3 in this regard).

Apart from the data interface 12, the control facility also comprises an examination unit 13, an interfering structure unit 14, a calculation unit 15, a reconstruction unit 16 and in this example also a position unit 17.

The examination unit 13 serves for defining an examination region U of a patient 6. Here a region is represented which could be suitable for an examination of the chest or the lungs. In a simple case the examination region can be defined by a manual input. However, the examination unit 13 can also define tools for demarcation of the examination region U in images or for defining the examination region U from specifications relating to the examination.

The interfering structure unit 14 defines a number of interfering structures S, with an interfering structure S being a structure which is located within the beam path of the computed tomography system 1 and reflecting or absorbing X-ray radiation with a strength outside of a tolerance range. It is possible to specify, for example, which structures in the human body are to be regarded as interfering structures S (for example the spinal column). It can then be ascertained which of these interfering structures S could interfere with a measurement of the examination region U. These are defined as the (relevant) interfering structures S.

The calculation unit 15 serves for calculating the beam paths of the X-rays R of a CT examination of the examination region U and for ascertaining interference angle ranges W of a gantry 2 of the computed tomography system at which beam paths run through an interfering structure S and the examination region U. With the known positions of the X-ray source 5, their known beam path and the known position of a defined interfering structure, such a calculation can be easily carried out geometrically.

As stated above, the data interface 12 serves for outputting control commands for carrying out a CT scan while the rotator 3 of the gantry 2 rotates, and for receiving CT data D.

With the reconstruction unit 16, an image dataset B can be reconstructed from the CT data D with the omission of ascertained interference angle ranges W.

The data interface 12 thereafter serves for outputting the reconstructed image dataset B.

In this example, the control facility 9 additionally comprises a position unit 17 designed for ascertaining a position of a positioning aid L. The position unit 17 is designed, in particular, to estimate the position on the basis of images and/or receive and evaluate the items of information of the positioning aid L.

Figure 2:
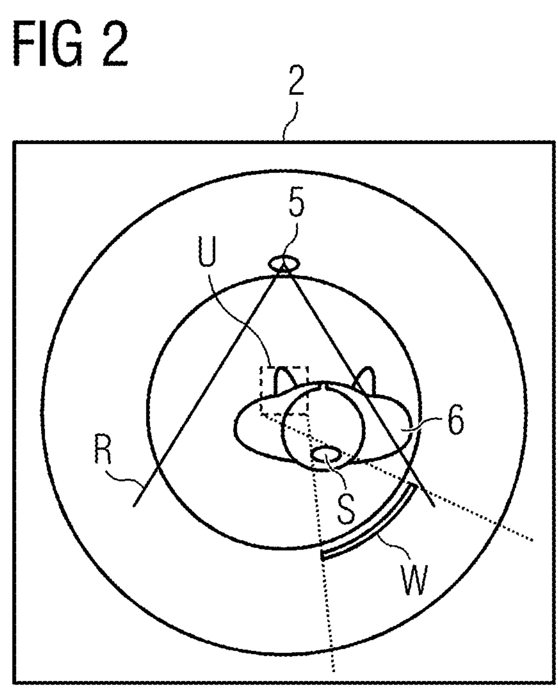
FIG. 2 shows an interfering structure and an interference angle range according to one or more example embodiments.

FIG. 2 shows an interfering structure S, here the spinal column, and an interference angle range W. It can be assumed that an observer along the axis of rotation of FIG. 1 is looking at the head of the patient 6. Here the patient 6 is positioned slightly eccentrically in the gantry 2, so the examination region U is located in the center around his left breast. The (actually invisible) spinal column is indicated here as an interfering structure S. The X-ray source 5 with its conical X-ray R is shown above the patient 6. During a scan it rotates around the patient 6. When it is located in the interference angle range W, X-rays R then firstly pass through the spinal column and then through the examination region U. This is undesirable and therefore the interference angle range W is omitted from the recording (or at least from the reconstruction).

FIG. 3 shows a sequence plan for one possible sequence of an inventive method for controlling a computed tomography system 1 as is represented, for example, in FIG. 1.

In step I, an examination region U of a patient 6 and an interfering structure S are defined. This interfering structure is the spinal column in this example, as shown in FIG. 2.

In step II, an interference angle range W of a gantry 2 of the computed tomography system 1 is ascertained by calculating the beam paths of the X-rays R, which run through an interfering structure S and the examination region U.

In step III, a CT scan is carried out while the gantry 2 rotates (that is to say, its rotator 3 rotates). CT data D is recorded in the process. It can be assumed that the X-ray source 5 is switched off in the interference angle range W in order to reduce the dose.

In step IV, an image dataset B is reconstructed from the CT data D with the omission of ascertained interference angle ranges W and is then output.

Figure 4:
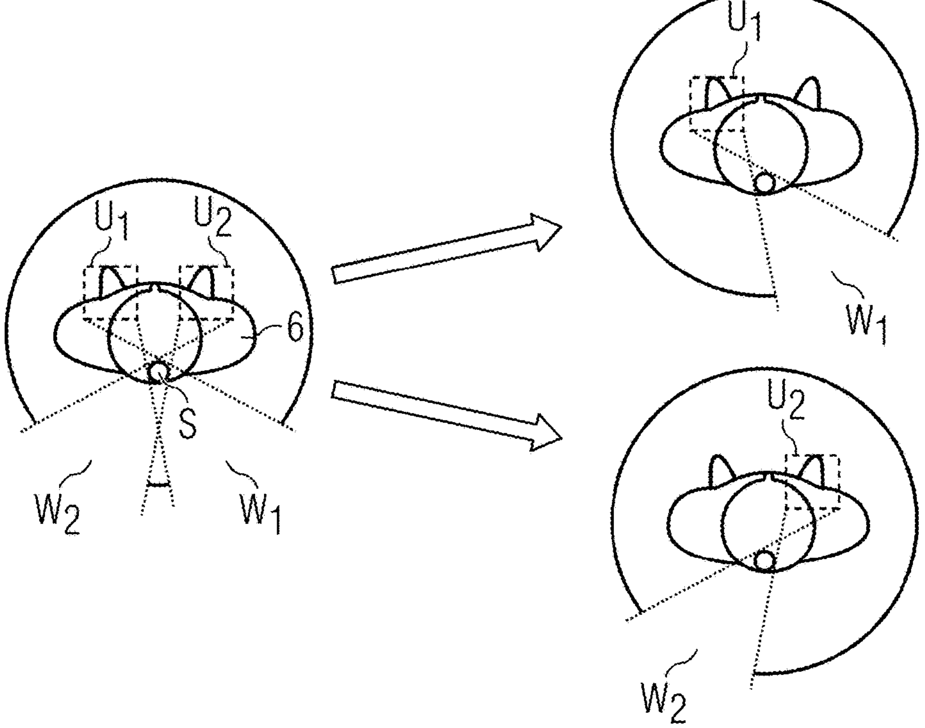
FIG. 4 shows an example of an inventive method for recording two examination regions.

FIG. 4 shows an example of an inventive method for recording. Two examination regions U1, U2 are defined on a patient 6 and interference angle ranges W1, W2 are separately ascertained for the two examination regions U1, U2. An interference angle range W1, W2 is associated with an examination region U1, U2 if beam paths run through an interfering structure S and the relevant examination region U1, U2. An image dataset B is then separately reconstructed for each examination region U1, U2 with the omission of ascertained interference angle ranges W1, W2 of the relevant examination region U1, U2.

In this case the interference angle ranges W1, W2 do not overlap. This means that the X-ray source is not switched off when recording the CT data since the data from 360° of the reconstruction can serve at least one of the examination regions U1, U2.

If there is an interference angle range W associated with both examination regions U1, U2 (an identical interference angle range W), then the X-ray source 5 used for recording could be switched off in this interference angle range W.

In conclusion it will once again be pointed out that the figures described in detail above are merely exemplary embodiments which can be modified in a wide variety of ways by a person skilled in the art without departing from the scope of the invention. Furthermore, use of the indefinite article "a" or "an" does not preclude the relevant features from also being present several times. Similarly, the terms "unit" and "device" do not preclude the relevant components from consisting of a plurality of sub-components which can potentially also be spatially distributed. The expression "a number" should be taken to mean "at least one". Independent of the grammatical term usage, individuals with male, female or other gender identities are included within the term.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "on," "connected," "engaged," "interfaced," and "coupled." Unless explicitly described as being "direct," when a relationship between first and second elements is described in the disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" on, connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

It is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed above. Although discussed in a particular manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments. The present invention may, however, be embodied in many alternate forms and should not be construed as limited to only the embodiments set forth herein.

In addition, or alternative, to that discussed above, units and/or devices according to one or more example embodiments may be implemented using hardware, software, and/or a combination thereof. For example, hardware devices may be implemented using processing circuity such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of f responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above.

Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particular manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one example embodiment relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one more modules. References to multiple microprocessors or encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

The invention claimed is:

1. A method for controlling a computed tomography system, the method comprising:

defining an examination region of an examination object;

defining a number of interfering structures, wherein an interfering structure is a structure located within a beam path of the computed tomography system and reflects or absorbs X-ray radiation with a strength outside of a tolerance range;

calculating beam paths of X-rays of a CT examination of the examination region and ascertaining interference angle ranges of a gantry of the computed tomography system at which the beam paths run through the interfering structure and the examination region;

carrying out a CT scan while the gantry rotates, and recording CT data;

reconstructing an image dataset from CT data of the recorded CT data excluding the ascertained interference angle ranges; and outputting the image dataset.

2. The method of claim 1, wherein the recording records the CT data for the gantry rotation excluding the ascertained interference angle ranges.

3. The method of claim 2, wherein the recording switches off an X-ray source in the ascertained interference angle ranges or at least a radiation power of the X-ray source is reduced.

4. The method of claim 3, wherein the recording includes,
   determining at least one of an acceleration voltage or a current strength of the X-ray source for the recording based on an entire angle range of 360° minus the interference angle ranges.

5. The method of claim 1, wherein at least one interference angle range is an angle range at which beams of an X-ray source of the gantry run firstly through at least one of the interfering structures and then through the examination region.

6. The method of claim 1, wherein the defining is based on a topogram of the examination object, a camera recording of the examination object or a model of the examination object.

7. The method of claim 1, wherein the examination object is positioned via a positioning aid or fixed with a fixation and the defining is based on a position and a form of the positioning aid or fixation.

8. The method of claim 7, wherein an isocenter of the examination region is defined after positioning of the examination object via the positioning aid.

9. The method of claim 1, wherein the ascertaining the interference angle ranges includes checking whether a remaining angle range of an angle range of 360° minus the interference angle ranges and additionally rotated about 180° has a continuous angle range of 360°.

10. The method of claim 9, wherein if the remaining angle range is less than 360°,
   simulated data, which simulates recordings in a missing angle range, is added to the CT data excluding the ascertained interference angle ranges before reconstruction of the image dataset, or
   a missing angle range is removed from the number of interference angle ranges, a degree of interference in the missing angle range and a degree of interference of an angle range rotated 180° are ascertained to remove from the interference angle ranges based on a comparison of the degree of interference in the missing angle range and the degree of interference of an angle range rotated 180°.

11. The method of claim 1, wherein two or more examination regions of the examination object are defined, interference angle ranges are separately ascertained for the two or more examination regions, wherein an interference angle range is associated with an examination region if beam paths run through an interfering structure and the associated examination region, and for each examination region an image dataset is separately reconstructed excluding the ascertained interference angle ranges of the associated examination region.

12. The method of claim 1, wherein the reconstructing includes using a combination of a data sparsity reconstruction technique with an iterative solution approach.

13. The method of claim 1, wherein the examination region is a chest or lungs and wherein the number of interfering structures includes a spinal column.

14. A non-transitory computer program product, comprising commands which, when executed by a computer, cause the computer to perform the method of claim 1, wherein carrying out a CT recording corresponds to a transmission of corresponding control commands and receiving of the recorded CT data.

15. A non-transitory computer-readable storage medium, comprising commands which, when executed by a computer, cause the computer to perform the method of claim 1, wherein carrying out a CT recording corresponds to a transmission of corresponding control commands and receiving of the recorded CT data.

16. A system for controlling a computed tomography system, the system comprising:
   at least one processor configured to cause the system to,
      define an examination region of an examination object,
      define a number of interfering structures, wherein an interfering structure is a structure located within a beam path of the computed tomography system and reflects or absorbs X-ray radiation with a strength outside of a tolerance range,
      calculate beam paths of X-rays of a CT examination of the examination region and ascertaining interference angle ranges of a gantry of the computed tomography system at which the beam paths run through the interfering structure and the examination region, and
      reconstruct an image dataset from CT data of received CT data excluding the ascertained interference angle ranges;
   a data interface configured to output control commands for carrying out a CT scan while the gantry rotates, and to receive CT data; and
   a data interface configured to output the image dataset.

17. The system of claim 16,
   wherein the at least one processor is further configured to ascertain a position of a positioning aid or a fixation, and at least one of estimate the position based on images or receive and evaluate items of information of the positioning aid.

18. The computed tomography system, further comprising:
   the system of claim 10.

* * * * *